US006783955B2

(12) United States Patent
Arvizu et al.

(10) Patent No.: US 6,783,955 B2
(45) Date of Patent: Aug. 31, 2004

(54) POLYNUCLEOTIDES ENCODING HUMAN PRESENILIN VARIANT

(75) Inventors: Chandra Arvizu, Menlo Park, CA (US); Lynn E. Murry, Fayetteville, AR (US); Matthew R. Kaser, Castro Valley, CA (US)

(73) Assignee: Incyte Corporation, Palo Alto, CA (US)

( * ) Notice: Subject to any disclaimer, the term of this patent is extended or adjusted under 35 U.S.C. 154(b) by 0 days.

(21) Appl. No.: 09/895,035

(22) Filed: Jun. 29, 2001

(65) Prior Publication Data

US 2002/0082211 A1 Jun. 27, 2002

Related U.S. Application Data

(63) Continuation-in-part of application No. 09/116,640, filed on Jul. 16, 1998.

(51) Int. Cl.[7] .......................... C12P 21/06; C12N 1/20; C12N 15/00; C12N 5/00; C07H 21/04

(52) U.S. Cl. ................ 435/69.1; 435/252.3; 435/320.1; 435/325; 536/23.1; 530/350; 530/300

(58) Field of Search ........................................ 536/23.1

(56) References Cited

U.S. PATENT DOCUMENTS 6,010,874 A * 1/2000 Hardy ......................... 30/312

OTHER PUBLICATIONS

Porter et al., Significance of Plasma Cytokine Levels in Melanoma Patients with Histologically Negative Sentinel Lymph Nodes, The Society of Surgical Oncology, Inc., 8:116–122, 2001.

Schellenberg, G.D., Genetic Dissection of Alzheimer Disease, a Heterogeneous Disorder, Natl. Acad. Sci. vol. 92, pp. 8552–8559, 1995.

Sherrington et al., Cloning of a Gene Bearing Missense Mutations in Early–onset Familial Alzheimer's Disease, Nature, vol. 375, pp. 754–760, 1995.

Levy–Lahad et al., Candidate Gene for the Chromosome 1 Familial Alzheimer's Disease Locus, Science, vol. 269, pp. 973–977, 1995.

Sahara et al., Identification and Characterization of Presenilin I–467, I–463 and I–374, FEBS, vol. 26, pp. 7–11, 1996.

Levitan et al., Assessment of Normal and Mutant Human Presenilin Function in Caenorhabditis Elegans, Proc. Natl. Acad. Sci., vol. 93, pp. 14940–14944, 1996.

* cited by examiner

*Primary Examiner*—Elizabeth Kemmerer
*Assistant Examiner*—Sharon Turner
(74) *Attorney, Agent, or Firm*—Incyte Corporation

(57) ABSTRACT

The invention provides a cDNA which encodes human presenilin variant. It also provides for the use of the cDNA and protein in the diagnosis, prognosis, treatment and evaluation of therapies for cancer or neurodegenerative or immune disorders. The invention further provides vectors and host cells for the production of the protein and transgenic model systems.

12 Claims, 7 Drawing Sheets

```
                10                  19                  28                  37                  46                  55
5' AAC CTG AGC TAC GAG CCG CGG CGG CAG CGG GGC GGC GGG GAA GCG TAT ACC TAA

                64                  73                  82                  91                 100                 109
   TCT GGG AGC CTG CAA GTG ACA ACA GCC TTT GCG GTC CTT AGA CAG CTT GGC CTG

               118                 127                 136                 145                 154                 163
   GAG GAG AAC ACA TGA AAG AAA GAA CCT CAA GAG GCT TTG TTT TCT GTG AAA CAG

               172                 181                 190                 199                 208                 217
   TAT TTC TAT ACA GTT GCT CCA ATG ACA GAG TTA CCT GCA CCG TTG TCC TAC TTC
                               M   T   E   L   P   A   P   L   S   Y   F

               226                 235                 244                 253                 262                 271
   CAG AAT GCA CAG ATG TCT GAG GAC AAC CAC CTG AGC AAT ACT AAT GAC AAT AGA
   Q   N   A   Q   M   S   E   D   N   H   L   S   N   T   N   D   N   R

               280                 289                 298                 307                 316                 325
   GAA CGG CAG GAG CAC AAC GAC AGA CGG AGC CTT GGC CAC CCT GAG CCA TTA TCT
   E   R   Q   E   H   N   D   R   R   S   L   G   H   P   E   P   L   S

               334                 343                 352                 361                 370                 379
   AAT GGA CGA CCC CAG GGT AAC TCC CGG CAG GTG GTG GAG CAA GAT GAG GAA GAA
   N   G   R   P   Q   G   N   S   R   Q   V   V   E   Q   D   E   E   E
```

FIGURE 1A

```
        388         397         406         415         424         433
GAT GAG GAG CTG ACA TTG AAA TAT GGC GCC AAG CAT GTG ATC ATG CTC TTT GTC
D   E   E   L   T   L   K   Y   G   A   K   H   V   I   M   L   F   V

        442         451         460         469         478         487
CCT GTG ACT CTC TGC ATG GTG GTG GTC GTG GCT ACC ATT AAG TCA GTC AGC TTT
P   V   T   L   C   M   V   V   V   V   A   T   I   K   S   V   S   F

        496         505         514         523         532         541
TAT ACC CGG AAG GAT GGG CAG CTA ATC TAT ACC CCA TTC ACA GAA GAT ACC GAG
Y   T   R   K   D   G   Q   L   I   Y   T   P   F   T   E   D   T   E

        550         559         568         577         586         595
ACT GTG GGC CAG AGA GCC CTG CAC TCA ATT CTG AAT GCT GCC ATC ATG ATC AGT
T   V   G   Q   R   A   L   H   S   I   L   N   A   A   I   M   I   S

        604         613         622         631         640         649
GTC ATT GTT GTC ATG ACT ATC CTC CTG GTG GTT CTG TAT AAA TAC AGG TGC TAT
V   I   V   V   M   T   I   L   L   V   V   L   Y   K   Y   R   C   Y

        658         667         676         685         694         703
AAG GTG AGC ATG AGA CAC AGA TCT TTG CTT TCC ACC CTG TTC TTC TTA TGG TTG
K   V   S   M   R   H   R   S   L   L   S   T   L   F   F   L   W   L
```

FIGURE 1B

```
     712         721         730         739         748         757
GGT ATT CTT GTC ACA GTA ACT TAA CTG ATC TAG GAA AGA AAA AAT GTT TTG TCT
 G   I   L   V   T   V   T
     766         775         784         793         802         811
TCT AGA GAT AAG TTA ATT TTT AGT TTT CTT CCT CCT CAT TGT GGA ACA TTC CAA

AAA AAA AA 3'
```

```
1    M T E L P A P L S Y F Q N A Q M S E D N H L S N T N D N R E R Q E H N D R R S L   p1353337
1    M T E L P A P L S Y F Q N A Q M S E D N H L S N T N D N R E R Q E H N D R R S L   GI 1244638

41   G H P E P L S N G R P Q G N S R Q V V E Q D E E E D E E L T L K Y G A K H V I M   p1353337
41   G H P E P L S N G R P Q G N S R Q V V E Q D E E E D E E L T L K Y G A K H V I M   GI 1244638

81   L F V P V T L C M V V V V A T I K S V S F Y T R K D G Q L I Y T P F T E D T E T   p1353337
81   L F V P V T L C M V V V V A T I K S V S F Y T R K D G Q L I Y T P F T E D T E T   GI 1244638

121  V G Q R A L H S I L N A A I M I S V I V V M T I L L V V L Y K Y R C Y K V S - -   p1353337
121  V G Q R A L H S I L N A A I M I S V I V V M T I L L V V L Y K Y R C Y K V I H A   GI 1244638

159  - M R H R S L L S T L F F - - L W L G - I L V T V T                               p1353337
161  W L I I S S L L L L F F F S F I Y L G E V F K T Y N                               GI 1244638
```

```
1    GAACCTGAGCTACGAGCCGCGGCGGCAGCGGGGCGGCGGG n1353337
1    ---------------------------------------- GI 1244637

41   GAAGCGTATACCTAATCTGGGAGCCTGCAAGTGACAACAG n1353337
1    ---------------------------------------- GI 1244637

81   CCTTTGCGGTCCTTAGACAGCTTGGCCTGGAGGAGAACAC n1353337
1    ---------------------------------------- GI 1244637

121  ATGAAAGAAAGAACCTCAAGAGGCTTTGTTTTCTGTGAAA n1353337
1    ---------------------------------------- GI 1244637

161  CAGTATTTCTATACAGTTGCTCCAATGACAGAGTTACCTG n1353337
1    ------------------------ATGACAGAGTTACCTG GI 1244637

201  CACCGTTGTCCTACTTCCAGAATGCACAGATGTCTGAGGA n1353337
17   CACCGTTGTCCTACTTCCAGAATGCACAGATGTCTGAGGA GI 1244637

241  CAACCACCTGAGCAATACTAATGACAATAGAGAACGGCAG n1353337
57   CAACCACCTGAGCAATACTAATGACAATAGAGAACGGCAG GI 1244637

281  GAGCACAACGACAGACGGAGCCTTGGCCACCCTGAGCCAT n1353337
97   GAGCACAACGACAGACGGAGCCTTGGCCACCCTGAGCCAT GI 1244637
```

FIGURE 3A

| | | |
|---|---|---|
| 321 | T A T C T A A T G G A C G A C C C C A G G G T A A C T C C C G G C A G G T G G T | n1353337 |
| 137 | T A T C T A A T G G A C G A C C C C A G G G T A A C T C C C G G C A G G T G G T | GI 1244637 |
| 361 | G G A G C A A G A T G A G G A A G A A G A T G A G G A G C T G A C A T T G A A A | n1353337 |
| 177 | G G A G C A A G A T G A G G A A G A A G A T G A G G A G C T G A C A T T G A A A | GI 1244637 |
| 401 | T A T G G C G C C A A G C A T G T G A T C A T G C T C T T T G T C C C T G T G A | n1353337 |
| 217 | T A T G G C G C C A A G C A T G T G A T C A T G C T C T T T G T C C C T G T G A | GI 1244637 |
| 441 | C T C T C T G C A T G G T G G T G G T C G T G G C T A C C A T T A A G T C A G T | n1353337 |
| 257 | C T C T C T G C A T G G T G G T G G T C G T G G C T A C C A T T A A G T C A G T | GI 1244637 |
| 481 | C A G C T T T T A T A C C C G G A A G G A T G G G C A G C T A A T C T A T A C C | n1353337 |
| 297 | C A G C T T T T A T A C C C G G A A G G A T G G G C A G C T A A T C T A T A C C | GI 1244637 |
| 521 | C C A T T C A C A G A A G A T A C C G A G A C T G T G G G C C A G A G A G C C C | n1353337 |
| 337 | C C A T T C A C A G A A G A T A C C G A G A C T G T G G G C C A G A G A G C C C | GI 1244637 |
| 561 | T G C A C T C A A T T C T G A A T G C T G C C A T C A T G A T C A G T G T C A T | n1353337 |
| 377 | T G C A C T C A A T T C T G A A T G C T G C C A T C A T G A T C A G T G T C A T | GI 1244637 |
| 601 | T G T T G T C A T G A C T A T C C T C C T G G T G G T T C T G T A T A A A T A C | n1353337 |
| 417 | T G T T G T C A T G A C T A T C C T C C T G G T G G T T C T G T A T A A A T A C | GI 1244637 |

FIGURE 3B

```
641 AGGTGCTATAAGGTGA-----GCATGAGACACAG----AT n1353337
457 AGGTGCTATAAGGTCATCCATGCCTGGCTTATTATATCAT GI 1244637

672 CTTTGCTTT--CCACCCTGTTCTTC--TTAT--GGTTGGG n1353337
497 CTCTATTGTTGCTGTTCTTTTTTTCATTCATTTACTTGGG GI 1244637

706 -----TATT-----CTTGTCACA-----GTAACTTA---- n1353337
537 GGAAGTGTTTAAAACCTATAACGTTGCTGTGGACTACATT GI 1244637

727 ACTG-----------ATCTAGGA---------------AA n1353337
577 ACTGTTGCACTCCTGATCTGGAATTTTGGTGTGGTGGGAA GI 1244637

741 ---------------GAAAAAAT--GTTTTGTCTTC--TA n1353337
617 TGATTTCCATTCACTGGAAAGGTCCACTTCGACTCCAGCA GI 1244637

762 GAGATA---------AGTTAAT----------TTTTAGTT n1353337
657 GGCATATCTCATTATGATTAGTGCCCTCATGGCCCTGGTG GI 1244637

783 TTCTTC------CTCCTC------ATTGTGGAAC------ n1353337
697 TTTATCAAGTACCTCCCTGAATGGACTGCGTGGCTCATCT GI 1244637

805 --------ATTCCAAAAAAAAAA                  n1353337
737 TGGCTGTGATTTCAGTATATGATTTAGTGGCTGT       GI 1244637
```

FIGURE 3C

POLYNUCLEOTIDES ENCODING HUMAN PRESENILIN VARIANT

This application is a continuation-in-part of U.S. Ser. No. 09/116,640, filed Jul. 16, 1998.

FIELD OF THE INVENTION

This invention relates to a human presenilin variant, its encoding cDNA and to the use of these molecules in the diagnosis, prognosis, treatment and evaluation of therapies for cancers and neurodegenerative and immune disorders, particularly early onset Alzheimer's disease.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Cancer and immune response as a complication of cancer are characterized by continuous cell proliferation, inflammation, and cell death. Several molecular pathways have been linked to these activities, their development and progression. In addition, the analysis of the differential expression of key genes in any of these pathways may be diagnostically or prognostically important. For example, the analysis of cytokine levels is known to be useful as a prognostic indicator for distinguishing between various histologically-similar melanomas (Porter et al. (2001) Ann Surg Oncol 8:116–122).

Alzheimer's disease (AD) is a degenerative disorder of the central nervous system which causes progressive memory loss and cognitive decline during mid to late adult life and is accompanied by a wide range of neuropathologic features including amyloid deposits and intra-neuronal neurofibrillary tangles. Although the pathogenic pathway leading to neurodegeneration and AD is not well understood, at least three genetic loci that confer genetic susceptibility to the disease have been identified. (Schellenberg, G. D. (1995) Proc. Natl. Acad. Sci. 92:8552–8559; Sherrington, R. et al. (1995) Nature 375:754–760.)

The $\epsilon$4 allele (C112 to R) of the apolipoprotein E gene is associated with AD in a significant proportion of late-onset (>60 years) cases. Mutations in the gene for the β-amyloid precursor protein (βAPP) have been found in a small number of families (<3% of cases) with disease onset before 56 years of age. A third locus (AD3) has been mapped by genetic linkage studies to chromosome 14q24.3 and may account for up to 70% of early-onset autosomal-dominant AD. (Sherrington et al. supra.) Although early-onset AD is less common than late-onset AD, the AD3 locus is associated with the most aggressive form of the disease.

Initial studies of known genes on chromosome 14q resulted in their exclusion from the AD3 locus. However, additional studies conducted in a collection of 21 pedigrees segregating AD as a putative autosomal dominant trait resulted in the selection of more than 18 genetic markers associated with the AD3 locus, and the isolation of at least 19 transcripts encoded within this region. (Sherrington et al. supra.) One of these transcripts (S182) was found to encode presenilin-I (PS-1 or 1–467) containing multiple transmembrane domains and resembling an integral membrane protein. A similar gene product (presenilin-II, PS-2) was also identified in association with chromosome 1 in a separate lineage of AD subjects. (Levy-Lahad, E. et al. (1995) Science 269:973–977.) In both PS-1 and PS-2, missense mutations were found that cosegregated with early-onset familial AD in the respective pedigrees. The fact that mutations occurred in conserved domains of the gene and were not found in normal, asymptomatic family members indicates that the mutations are pathogenic for this form of AD. (Sherrington et al. supra; Levy-Lahad et al. supra.) In all cases, the mutations were found in the putative open reading frame of the nucleotide and would be predicted to change the encoded amino acid at that position. Variants of normal human presenilin (PS; 1467, 1463, and 1374) have also been reported. These variants result from either nucleotide deletions or alternative splicing, are ubiquitously expressed, and are associated with intracellular membranes. (Sahara, N. et al. (1996) FEBS Lett. 26:7–11.)

The normal cellular function of PS and, more particularly, the effects of these mutations on cellular function in AD individuals is not yet known. However, the general topology of PS suggests that it is an integral membrane protein such as a receptor, channel protein, or structural membrane protein. In addition, similarities between PS and the *Caenorhabditis elegans* proteins, SPE-4 and SEL-12, suggest that they may have similar functions. SPE-4 appears to be involved in the transport and storage of soluble and membrane-bound polypeptides during membrane budding and fusion events in *C. elegans*. (Sherrington et al. supra.) In humans, PS could be involved in similar vesicle transport processes, perhaps in moving βAPP. If so, mutations in PS could alter intracellular trafficking of βAPP and ultimately lead to altered βAPP processing. (Levy-Lahad et al. supra.) Studies using PS-1 and PS-2 and their AD-linked mutations to rescue the effects of a sel-12 mutant in *C. elegans* demonstrated that mutant human presenilins had reduced ability to rescue the sel-12 mutation relative to PS-1 and PS-2. (Levitan, D et al. (1996) Proc. Natl. Acad. Sci. 93:14940–14944.) The results indicated that the mutant PSs have reduced activity relative to normal PS-1 and PS-2 and that this may be a contributing factor in the development of AD. It was also noted by Levy-Lahad (supra) that several of the amino acid mutations occurring in AD-associated PS were found at or near the beginning of transmembrane domains, and that the mutations may adversely effect the insertion or anchoring of these proteins in the membrane.

The discovery of a human presenilin variant and its encoding cDNA satisfies a need in the art by providing new compositions which are useful in the diagnosis, prognosis, treatment and evaluation of therapies for cancers and neurodegenerative and immune disorders, particularly early onset Alzheimer's disease.

SUMMARY OF THE INVENTION

The present invention is based on the discovery of a human presenilin variant and its encoding cDNA that are differentially expressed in human disorders. The cDNA, protein and an antibody which specifically binds the protein are useful in the diagnosis, prognosis, treatment and evaluation of therapies for cancers and neurodegenerative and immune disorders, particularly early onset Alzheimer's disease.

The invention provides an isolated cDNA comprising a nucleic acid sequence encoding a protein having the amino acid sequence of SEQ ID NO:1. The invention also provides an isolated cDNA selected from a nucleic acid sequence of SEQ ID NO:2, a fragment of SEQ ID NO:2 selected from SEQ ID NOs:3–7, and a variant selected from SEQ ID NOs:8–11 which has from about 85% to about 91% sequence identity with SEQ ID NO:2, and complements of SEQ ID NOs:2–11. The invention additionally provides compositions, a substrate, and a probe comprising the cDNA or the complement of the cDNA. The invention further provides a vector containing the cDNA, a host cell containing the vector and a method for using the cDNA to make the human presenilin variant. The invention still further provides a transgenic cell line or organism comprising the vector containing a cDNA selected from SEQ ID NO:2–11. The invention additionally provides a fragment, a variant, or the complement of a cDNA selected from SEQ ID NOs:2–11. In one aspect, the invention provides a substrate containing at least one cDNA selected from SEQ ID NOs:2–11 or a complement thereof. In a second aspect, the invention provides a cDNA or the complement thereof which can be used in methods of detection, screening, and purification. In a further aspect, the cDNA is a single-stranded RNA or DNA molecule, a peptide nucleic acid, a branched nucleic acid and the like.

The invention provides a method for using a cDNA to detect differential expression of a nucleic acid in a sample comprising hybridizing a cDNA to the nucleic acids, thereby forming hybridization complexes and comparing hybridization complex formation with at least one standard, wherein the comparison indicates differential expression of the cDNA in the sample. In one aspect, the method of detection further comprises amplifying the nucleic acids of the sample prior to hybridization. In another aspect, the method showing differential expression of the cDNA is used to diagnose transitional cell carcinoma of the bladder and early onset Alzheimer's disease. In yet another aspect, the cDNA or a fragment or a variant or the complements thereof may comprise an element on an array.

The invention additionally provides a method for using a cDNA or a fragment or a variant or the complements thereof to screen a library or plurality of molecules or compounds to identify or purify at least one ligand which specifically binds the cDNA, the method comprising combining the cDNA with the molecules or compounds under conditions allowing specific binding, and detecting specific binding to the cDNA, thereby identifying or purifying a ligand which specifically binds the cDNA. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified protein or a portion thereof selected from the group consisting of an amino acid sequence of SEQ ID NO:1, a variant of SEQ ID NO:1, an antigenic epitope of SEQ ID NO:1, and a biologically active portion of SEQ ID NO:1. The invention also provides a composition comprising the purified protein and a labeling moiety or a pharmaceutical carrier. The invention further provides a method of using the human presenilin variant to treat a subject with cancer or a neurodegenerative or immune disorders comprising administering to a patient in need of such treatment the composition containing the purified protein. The invention still further provides a method for using a protein to screen a library or a plurality of molecules or compounds to identify or purify at least one ligand, the method comprising combining the protein with the molecules or compounds under conditions to allow specific binding and detecting specific binding, thereby identifying or purifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with a cancer or a neurodegenerative or immune disorder.

The invention provides a method of using a protein to screen a subject sample for antibodies which specifically bind the protein comprising isolating antibodies from the subject sample, contacting the isolated antibodies with the protein under conditions to form an antibody:protein complex, dissociating the antibody from the protein, and comparing the quantity of antibody with known standards, wherein the presence or quantity of antibody is diagnostic of a cancer or neurodegenerative or immune disorders.

The invention also provides a method of using a protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which binds specifically to a protein which is expressed in cancers and neurodegenerative and immune disorders, particularly early onset Alzheimer's disease. The invention also provides a method of using an antibody to diagnose a particular cancer or neurodegenerative disorder comprising combining the antibody comparing the quantity of bound antibody to known standards, thereby establishing the presence of the particular cancer or neurodegenerative disorder. The invention further provides a method of using an antibody to treat and immune and neurodegenerative disorders comprising administering to a patient in need of such treatment a composition comprising the purified antibody and a pharmaceutical carrier.

The invention provides a method for inserting a heterologous marker gene into the genomic DNA of a mammal to disrupt the expression of the endogenous polynucleotide. The invention also provides a method for using a cDNA to produce a mammalian model system, the method comprising constructing a vector containing the cDNA of SEQ ID NO:8–1 1, transforming the vector into an embryonic stem cell, selecting a transformed embryonic stem cell, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES

FIGS. 1A, 1B, and 1C shows the amino acid sequence (SEQ ID NO:1) and nucleic acid sequence (SEQ ID NO:2) of human presenilin variant. The alignment was produced using MACDNASIS PRO software (Hitachi Software Engineering, South San Francisco Calif.).

FIG. 2 shows the amino acid sequence alignments between human presenilin variant (p1353337; SEQ ID NO:1) and human presenilin, 1–463 (g1244638; SEQ ID NO:12) produced using the MEGALIGN program (DNASTAR, Madison Wis.). SEQ ID NO:12 has been truncated to display the alignment of human presenilin variant with residues 1 to 186 of SEQ ID NO:12.

FIGS. 3A, 3B, and 3C show the nucleic acid sequence alignments between the nucleic acid sequence of human presenilin variant (n1353337; SEQ ID NO:2) and the nucleic acid sequence of human presenilin, 1–463 (g1244637; SEQ ID NO: 13) produced using the MEGALIGN program (DNASTAR). SEQ ID NO:13 has been truncated to display alignment with nucleotides 1 to 770 of SEQ ID NO:2.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"Array" refers to an ordered arrangement of at least two cDNAs or antibodies on a substrate. At least one of the cDNAs or antibodies represents a control or standard, and the other, a cDNA or antibody of diagnostic or therapeutic interest. The arrangement of two to about 40,000 cDNAs or of two to about 40,000 monoclonal or polyclonal antibodies on the substrate assures that the size and signal intensity of each labeled hybridization complex, formed between each cDNA and at least one nucleic acid, or antibody:protein complex, formed between each antibody and at least one protein to which the antibody specifically binds, is individually distinguishable.

"Human presenilin variant" refers to a purified protein obtained from any mammalian species, including bovine, canine, murine, ovine, porcine, rodent, simian, and preferably the human species, and from any source, whether natural, synthetic, semi-synthetic, or recombinant.

The "complement" of a cDNA of the Sequence Listing refers to a nucleic acid molecule which is completely complementary to the cDNA over its full length and which will hybridize to the cDNA or an mRNA under conditions of maximal stringency.

"cDNA" refers to an isolated polynucleotide, nucleic acid molecule, or any fragment or complement thereof. It may have originated recombinantly or synthetically, may be double-stranded or single-stranded, represents coding and noncoding 3' or 5' sequence, and generally lacks introns.

A "composition" refers to the polynucleotide and a labeling moiety, a purified protein and a pharmaceutical carrier, an antibody and a labeling moiety, and the like.

"Derivative" refers to a cDNA or a protein that has been subjected to a chemical modification. Derivatization of a cDNA can involve substitution of a nontraditional base such as queosine or of an analog such as hypoxanthine. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased or upregulated or a decreased or downregulated expression as detected by presence, absence or at least two-fold change in the amount or abundance of a transcribed messenger RNA or translated protein in a sample.

"Disorder" refers to conditions, diseases or syndromes in which the cDNAs and human presenilin variant are differentially expressed. Such disorders include, but are not limited to, Alzheimer's disease, senile dementia, Huntington's disease, and schizophrenia; cancers, such as adenocarcinoma, lymphoma, and sarcoma, and, in particular, ductal adenocarcinoma of the breast, leiomyoma of the uterus, myxoid liposarcoma of the lung, myxoma of the heart, seminoma of the testis, transitional cell carcinoma of the bladder, and immune disorders such as Crohn's disease and rheumatoid arthritis.

"Fragment" refers to a chain of consecutive nucleotides from about 50 to about 4000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. Hybridization conditions, degree of complementarity and the use of nucleotide analogs affect the efficiency and stringency of hybridization reactions.

"Labeling moiety" refers to any visible or radioactive label than can be attached to or incorporated into a cDNA or protein. Visible labels include but are not limited to anthocyanins, green fluorescent protein (GFP), β glucuronidase, luciferase, Cy3 and Cy5, and the like. Radioactive markers include radioactive forms of hydrogen, iodine, phosphorous, sulfur, and the like.

"Ligand" refers to any agent, molecule, or compound which will bind specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers a single-stranded molecule from about 18 to about 60 nucleotides in length which may be used in hybridization or amplification technologies or in regulation of replication, transcription or translation. Equivalent terms are amplimer, primer, and oligomer.

An "oligopeptide" is an amino acid sequence from about five residues to about 15 residues that is used as part of a fusion protein to produce an antibody.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single-stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR).

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Similarity" refers to the quantification (usually percentage) of nucleotide or residue matches between at least two sequences aligned using a standard algorithm such as Smith-Waterman alignment (Smith and Waterman (1981) J Mol Biol 147:195–197) or BLAST2 (Altschul et a. (1997) Nucleic Acids Res 25:3389–3402). BLAST2 may be used in a reproducible way to insert gaps in one of the sequences in order to optimize alignment and to achieve a more meaningful comparison between them. Particularly in proteins, similarity is greater than identity in that conservative substitutions (for example, valine for leucine or isoleucine) are counted in calculating the reported percentage. Substitutions which are considered to be conservative are well known in the art.

"Specific binding" refers to a special and precise interaction between two molecules which is dependent upon their structure, particularly their molecular side groups. For example, the intercalation of a regulatory protein into the major groove of a DNA molecule or the binding between an epitope of a protein and an agonist, antagonist, or antibody.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "transcript image" is a profile of gene transcription activity in a particular tissue at a particular time.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

The Invention

The invention is based on the discovery of a human presenilin variant and its encoding cDNA and on the use of the cDNA, or fragments thereof, and protein, or portions thereof, directly or as compositions for the diagnosis, prognosis, treatment and evaluation of therapies for cancers, neurodegenerative and immune disorders, particularly early-onset Alzheimer's disease.

Nucleic acids encoding the human presenilin variant of the present invention were first identified in Incyte Clone 1353337 from the heart, atrium myxoma cDNA library (LATRTUT02) using a computer search, e.g., BLAST, for amino acid sequence alignments. A consensus sequence, SEQ ID NO:2, was derived from the following overlapping and/or extended nucleic acid sequences: Incyte Clones 991723R6 (COLNNOT11), 1353337H1, 1353337T6, and 1353337F6 (LATRTUT02) and 3555771H1 (LUNGNOT31) which are SEQ ID NOs:3–7, respectively.

In one embodiment, the invention encompasses a protein comprising the amino acid sequence of SEQ ID NO:1, as shown in FIGS. 1A, 1B, and 1C. Human presenilin variant is 180 amino acids in length and has potential phosphorylation sites for casein kinase II at residue $T_{103}$ and for protein kinase C at $T_{70}$, $T_{95}$, $T_{103}$, and $S_{158}$. An HMM based analysis for transmembrane domains identified two regions of human presenilin variant from about residue $V_{85}$ to $F_{101}$ and from about residue $L_{130}$ to $V_{148}$ as potential transmembrane domains. As shown in FIG. 2, human presenilin variant has chemical and structural similarity with human presenilin 1–463 (g1244638; SEQ ID NO: 12). In particular, human presenilin variant and human presenilin 1–463 share 89% identity and the four potential phosphorylation sites found in human presenilin variant. As described in the GenBank record for presenilin 1 (g1709856, SEQ ID NO: 14), human presenilin variant is characterized by 1) two transmembrane domains, residues $N_{131}$ and $M_{142}$ which correspond to two of the proposed sites for missense mutations, 2) the $S_{169}$ conversion to $L_{169}$ dominant mutation, and 3) the $T_{143}$ and $R_{162}$ dominant mutations of human presenilin 1–463. These variations are particularly ascribed to early onset Alzheimer's disease. Furthermore, the residues for the splicing region which follows T25 in normal presenilin, V26, R27, S28, and Q29, are missing in the variant and in presenilin I-463 (SEQ ID NO:12) as shown in FIG. 2. As shown in FIGS. 3A, 3B, and 3C, the nucleic acid sequence of human presenilin variant (SEQ ID NO:2) has chemical and structural similarity with that of human presenilin 1–463 (g1244637; SEQ ID NO:13). In particular, the two sequences share 66% identity. The sequence encoding human presenilin variant differs significantly from that for human presenilin 1–463 by the presence of a 5'-UTR extending from nucleotide 1 to nucleotide 184 in human presenilin variant. In addition, the two sequences differ significantly in the 3' region of the molecule extending from about nucleotide 656 of human presenilin variant to the end of the molecule. The fragment of SEQ ID NO:2 from about nucleotide 656 to about nucleotide 724 encodes a fragment of SEQ ID NO: 1 from about amino acid residue $S_{158}$ at about amino acid residue $T_{180}$ and is useful, for example, as a hybridization probe. Northern analysis shows the expression of this sequence in various libraries and of particular note is the expression of human presenilin variant in endocrine and neurological tissues.

Mammalian variants of the cDNAs encoding the presenilin variant were identified using BLAST2 with default parameters and the ZOOSEQ cDNA library databases (Incyte Genomics, Palo Alto Calif.). These preferred variants have from about 85% to about 91% amino acid sequence identity to the human protein as shown in the table below. The first column shows the SEQ IDH for the human cDNA; the second column, the SEQ IDvAR for variant cDNAs; the third column, the sequence numbers for the variants; the fourth column, the species; the fifth column, percent identity to the human cDNA; and the sixth column, the nucleotide alignment (NtH) of the human and variant cDNAs.

| SEQ $ID_H$ | SEQ $ID_{VAR}$ | Sequence No. | Species | Identity | $Nt_H$ Alignment |
|---|---|---|---|---|---|
| 2 | 8 | 702764613H1 | Dog | 85% | 383–477, 583–612 |
| 2 | 9 | 055263_Mm.1 | Mouse | 86% | 108–199 |
| 2 | 10 | 701725602H1 | Rat | 91% | 365–531 |
| 2 | 11 | 701529589H1 | Rat | 91% | 92–147 |

The mammalian variants were isolated from the following ZOOSEQ cDNA libraries: SEQ ID NO:8 (CNLIUNN01; dog liver); SEQ ID NO:9 (MOLUDIT08; mouse lung sensitized with ovalbumin); SEQ ID NO:10 (RALIUNT15; rat liver); and SEQ ID NO: 11 (RADRNOT01; rat bladder).

It will be appreciated by those skilled in the art that as a result of the degeneracy of the genetic code, a multitude of cDNAs encoding human presenilin variant, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring human presenilin variant, and all such variations are to be considered as being specifically disclosed.

The cDNAs of SEQ ID NOs:2–11 may be used in hybridization, amplification, and screening technologies to identify and distinguish among SEQ ID NO:2 and related molecules in a sample. The mammalian cDNAs, SEQ ID NOs:8–11, may be used to produce transgenic cell lines or organisms which are model systems for human disorders including cancer and neurodegenerative disorders and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and use of the Invention cDNA Libraries

In a particular embodiment disclosed herein, mRNA is isolated from mammalian cells and tissues using methods which are well known to those skilled in the art and used to prepare the cDNA libraries. The Incyte cDNAs were isolated from mammalian cDNA libraries prepared as described in the EXAMPLES. The consensus sequences are chemically and/or electronically assembled from fragments including Incyte cDNAs and extension and/or shotgun sequences using computer programs such as PHRAP (P Green, University of Washington, Seattle Wash.), and the AUTOASSEMBLER application (Applied Biosystems (ABI), Foster City Calif.). After verification of the 5' and 3' sequence, at least one of the representative cDNAs which encode the human presenilin variant is designated a reagent. These reagent cDNAs are also used in the construction of human LIFEARRAYS (Incyte Genomics) and are represented among the sequences on the Human Genome Gem 1 array (Incyte Genomics).

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (ABI), the MEGABACE 1000 DNA sequencing system (APB), and the like. The sequences may be analyzed using a variety of algorithms well known in the art and described in Ausubel et al. (1997*; Short Protocols in Molecular Biology*, John Wiley & Sons, New York N.Y., unit 7.7) and in Meyers (1995*; Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences, including vector or chimeric sequences, or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (ABI), nested primers, and commercially available cDNA or genomic DNA libraries may be used to extend the nucleic acid sequence. For all PCR-based methods, primers may be designed using commercially available software to be about 22 to 30 nucleotides in length, to have a GC content of about 50% or more, and to anneal to a target molecule at temperatures from about 55 C. to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the human presenilin variant, allelic variants, or related molecules. The probe may be DNA or RNA, may be single-stranded, and should have at least 50% sequence identity to a nucleic acid sequence selected from SEQ ID NOs:2–11. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits.

The stringency of hybridization is determined by G+C content of the probe, salt concentration, and temperature. In particular, stringency can be increased by reducing the concentration of salt or raising the hybridization temperature. Hybridization can be performed at low stringency with buffers, such as 5× SSC with 1% sodium dodecyl sulfate (SDS) at 60 C., which permits the formation of a hybridization complex between nucleic acid sequences that contain some mismatches. Subsequent washes are performed at higher stringency with buffers such as 0.2× SSC with 0.1% SDS at either 45 C. (medium stringency) or 68 C. (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of detergents such as Sarkosyl or TRITON X-100 (Sigma-Aldrich, St Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays incorporating cDNAs or antibodies may be prepared and analyzed using methods well known in the art. Oligonucleotides or cDNAs may be used as hybridization probes or targets to monitor the expression level of large numbers of genes simultaneously or to identify genetic variants, mutations, and single nucleotide polymorphisms. Monoclonal or polyclonal antibodies may be used to detect or quantify expression of a protein in a sample. Such arrays may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Heller et al. (1997) Proc Natl Acad Sci 94:2150–2155; Heller et al. (1997) U.S. Pat. No. 5,605,662; and deWildt et al. (2000) Nature Biotechnol 18:989–994.)

Hybridization probes are also useful in mapping the naturally occurring genomic sequence. The probes may be hybridized to a particular chromosome, a specific region of a chromosome, or an artificial chromosome construction. Such constructions include human artificial chromosomes (HAC), yeast artificial chromosomes (YAC), bacterial artificial chromosomes (BAC), bacterial P1 constructions, or the cDNAs of libraries made from single chromosomes.

Expression

Any one of a multitude of cDNAs encoding the human presenilin variant may be cloned into a vector and used to express the protein, or portions thereof, in host cells. The nucleic acid sequence can be engineered by such methods as DNA shuffling, as described in U.S. Pat. No. 5,830,721, and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers may be propagated using culture techniques. Visible markers are also used to estimate the amount of protein expressed by the introduced genes. Verification that the host cell contains the desired cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6× His, FLAG, MYC, and the like. GST and 6× His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds a-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. These processes are described in the Novabiochem 1997/98 Catalog and Peptide Synthesis Handbook (San Diego Calif. pp. S1–S20). Automated synthesis may also be carried out on machines such as the ABI 431A peptide synthesizer (ABI). A protein or portion thereof may be purified by preparative high performance liquid chromatography and its composition confirmed by amino acid analysis or by sequencing (Creighton (1984) Proteins, Structures and Molecular Properties, WH Freeman, New York N.Y.).

Preparation and Screening of Antibodies

Various hosts including, but not limited to, goats, rabbits, rats, mice, and human cell lines may be immunized by injection with human presenilin variant or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:31–42; Cote et al. (1983) Proc Natl Acad Sci 80:2026–2030; and Cole et al. (1984) Mol Cell Biol 62:109–120.)

Alternatively, techniques described for antibody production may be adapted, using methods known in the art, to produce epitope-specific, single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The human presenilin variant, or a portion thereof, may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) Immunochemical Protocols, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

Nucleic Acid Assays

The cDNAs, fragments, oligonucleotides, complementary RNA and DNA molecules, and PNAs may be used to detect and quantify differential gene expression for diagnostic purposes. Disorders associated with differential expression of SEQ ID NO:2 specifically include early onset Alzheimer's disease. The diagnostic assay may use hybridization or quantitative PCR to compare gene expression in a biological sample from a patient to standard samples in order to detect differential gene expression. Qualitative and quantitative methods for this comparison are commercially available and well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Protein Assays

Detection and quantification of a protein using either labeled amino acids or specific polyclonal or monoclonal antibodies which specifically bind the protein are known in the art. Examples of such techniques include two-dimensional polyacrylamide gel electrophoresis, enzyme-linked immunosorbent assays (ELISAs), radioimmunoassays (RIAs), and fluorescence activated cell sorting (FACS). These assays and their quantitation against purified, labeled standards are well known in the art (Ausubel, supra, unit 10.1–10.6). A two-site, monoclonal-based immunoassay utilizing monoclonal antibodies reactive to two non-interfering epitopes is preferred, but a competitive binding assay may be employed. (See, e.g., Coligan et al. (1997) Current Protocols in Immunology, Wiley-Interscience, New York N.Y.; and Pound, supra.)

Therapeutics

As described in THE INVENTION section, chemical and structural similarity, in particular the sequence, specific motifs, or domains such as the RGD and coiled coil, exist between regions of the human presenilin variant (SEQ ID NO:1) and human presenilin 1–463 (SEQ ID NO:12) shown in FIG. 2. Residues $N_{131}$ and $M_{142}$ which correspond to missense mutations, the $S_{169}$ conversion to $L_{169}$ dominant mutation, and the $T_{143}$ and $R_{162}$ dominant mutations are shared with presenilin 1 affirm its association with early onset AD. In addition, differential expression is highly associated with transitional cell carcinoma of the bladder, the transcript image for which shown in EXAMPLE VIII. The human presenilin variant clearly plays a role in cancers and neurodegenerative and immune disorders.

In the treatment of cancer which is associated with the increased expression of the protein, it may be desirable to decrease protein expression or activity. In one embodiment, the an inhibitor, antagonist or antibody which specifically binds the protein may be administered to a subject to treat a condition associated with increased expression or activity. In another embodiment, a pharmaceutical composition comprising an inhibitor, antagonist, or antibody and a pharmaceutical carrier may be administered to a subject to treat a condition associated with the increased expression or activity of the endogenous protein. In an additional embodiment, a vector expressing the complement of the cDNA or fragments thereof may be administered to a subject to treat the disorder.

Any antisense molecules or vectors delivering these molecules may be administered in combination with other therapeutic agents. Selection of the agents for use in combination therapy may be made by one of ordinary skill in the art according to conventional pharmaceutical principles. A combination of therapeutic agents may act synergistically to affect treatment of a particular cancer at a lower dosage of each agent alone.

Modification of Gene Expression Using Nucleic Acids

Gene expression may be modified by designing complementary or antisense molecules (DNA, RNA, or PNA) to the control, 5', 3', or other regulatory regions of the gene encoding human presenilin variant. Oligonucleotides designed to inhibit transcription initiation are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, or the modification of adenine, cytidine, guanine, thymine, and uridine with acetyl-, methyl-, thio-groups renders the molecule less available to endogenous endonucleases.

Screening and Purification Assays

The cDNA encoding human presenilin variant may be used to screen a library or a plurality of molecules or compounds for specific binding affinity. The libraries may be aptamers, DNA molecules, RNA molecules, PNAs, peptides, proteins such as transcription factors, enhancers, or repressors, and other ligands which regulate the activity, replication, transcription, or translation of the endogenous gene. The assay involves combining a polynucleotide with a library or plurality of molecules or compounds under conditions allowing specific binding, and detecting specific binding to identify at least one molecule which specifically binds the single-stranded or double-stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a commercially available reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein or a portion thereof to purify a ligand would involve combining the protein or a portion thereof with a sample under conditions to allow specific binding, detecting specific binding between the protein and ligand, recovering the bound protein, and using a chaotropic agent to separate the protein from the purified ligand.

In a preferred embodiment, human presenilin variant may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands, and the specificity of binding or formation of complexes between the expressed protein and the ligand can be measured. Depending on the particular kind of molecules or compounds being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein. Molecules or compounds identified by screening may be used in a mammalian model system to evaluate their toxicity, diagnostic, or therapeutic potential.

Pharmacology

Pharmaceutical compositions contain active ingredients in an effective amount to achieve a desired and intended purpose and a pharmaceutical carrier. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

I cDNA Library Construction

LATRTUT02 cDNA Library Construction

The LATRTUT02 cDNA library was constructed from a myxoma removed from the left atrium of the heart from a 43-year-old Caucasian male who had undergone annuloplasty following diagnosis of atrial myxoma. The frozen tissue was homogenized and lysed using a POLYTRON homogenizer (Brinkmann Instruments, Westbury N.Y.) in guanidinium isothiocyanate solution. The lysate was centrifuged over a 5.7 M CsCl cushion using an SW28 rotor in an L8-70M ultracentrifuge (Beckman Coulter, Fullerton Calif.) for 18 hours at 25,000 rpm and ambient temperature. The RNA was extracted with acid phenol, pH 4.7, precipitated using 0.3 M sodium acetate and 2.5 volumes of ethanol, resuspended in RNAse-free water, and treated with DNAse at 37 C. The RNA extraction and precipitation were repeated. The mRNA was isolated with the OLIGOTEX kit (Qiagen, Chatsworth Calif.) and used to construct the cDNA library.

The mRNA was handled according to the recommended protocols in the SUPERSCRIPT plasmid system (Life Technologies). The cDNAs were fractionated on a SEPHAROSE CL4B column (Amersham Pharmacia Biotech), and those cDNAs exceeding 400 bp were ligated into pINCY 1 (Incyte Genomics). The plasmids were subsequently transformed into DH5α competent cells (Life Technologies).

II Isolation and Sequencing of cDNA Clones

Plasmid DNA was released from the host cells and purified using the REAL PREP 96 plasmid kit (Qiagen). The kit consists of a 96 well-block with reagents for 960 purifications. The recommended protocol was employed except for the following changes: 1) the 96 wells were each filled with only 1 ml of sterile TERRIFIC BROTH (BD Biosciences, Sparks Md.) with carbenicillin at 25 mg/l and glycerol at 0.4%; 2) after inoculation, the bacteria were cultured for 24 hours and then lysed with 60 μl of lysis buffer; and 3) the block was centrifuged at 2900 rpm for 5 min in the GS-6R centrifuge (Beckman Coulter) before the contents of the block were added to the primary filter plate. An optional step of adding isopropanol to Tris buffer was not routinely performed. After the last step in the protocol, samples were transferred to a 96-well block for storage.

III Sequencing and Analysis

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 373 or 377 sequencing system (ABI) or the MEGABACE 1000 DNA sequencing system (APB). Most of the isolates were sequenced according to standard ABI protocols and kits with solution volumes of 0.25×–1.0× concentrations. In the alternative, cDNAs were sequenced using solutions and dyes from APB.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using commercially available primer analysis software to be about 22 to 30 nucleotides in length, to have a GC content of about 50% or more, and to anneal to the target sequence at temperatures of about 68 C. to about 72 C. Any stretch of nucleotides that would result in hairpin structures and primer—primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and P-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C., three min; Step 2: 94 C., 15 sec; Step 3: 60 C., one min; Step 4: 68 C., two min; Step 5: Steps 2, 3, and 4 repeated 20 times; Step 6: 68 C., five min; Step 7: storage at 4 C. In the alternative, the parameters for primer pair T7 and SK+(Stratagene) were as follows: Step 1: 94 C., three min; Step 2: 94 C., 15 sec; Step 3: 57 C., one min; Step 4: 68 C., two min; Step 5: Steps 2, 3, and 4 repeated 20 times; Step 6: 68 C., five min; Step 7: storage at 4 C.

The concentration of DNA in each well was determined by dispensing 100 μl PICOGREEN quantitation reagent (0.25% reagent in 1× TE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy, Finland) to measure the fluorescence of the sample and to quantify the concentration of DNA. A 5 μl to 10 μl aliquot of the reaction mixture was analyzed by electrophoresis on a 1% agarose minigel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC 18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC 18 vector (APB), treated with Pfu DNA polymerase (Stratagene) to fill-in restriction site overhangs, and transfected into *E. coli* competent cells. Transformed cells were selected on antibiotic-containing media, and individual colonies were picked and cultured overnight at 37 C. in 384-well plates in LB/2× carbenicillin liquid media.

The cells were lysed, and DNA was amplified using primers, Taq DNA polymerase (APB) and Pfu DNA polymerase (Stratagene) with the following parameters: Step 1: 94 C., three min; Step 2: 94 C., 15 sec; Step 3: 60 C., one min; Step 4: 72 C., two min; Step 5: steps 2, 3, and 4 repeated 29 times; Step 6: 72 C., five min; Step 7: storage at 4 C. DNA was quantified using PICOGREEN quantitation reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the PRISM BIGDYE terminator cycle sequencing kit (ABI).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST2 to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the stringency for an exact match was set from a lower limit of about 40 (with 1–2% error due to uncalled bases) to a 100% match of about 70.

The BLAST software suite (NCBI, Bethesda Md.; http://www.ncbi.nlm.nih.gov/gof/bl2.html), includes various sequence analysis programs including "blastn" that is used to align nucleotide sequences and BLAST2 that is used for direct pairwise comparison of either nucleotide or amino acid sequences. BLAST programs are commonly used with gap and other parameters set to default settings, e.g.: Matrix:

BLOSUM62; Reward for match: 1; Penalty for mismatch: 2; Open Gap: 5 and Extension Gap: 2 penalties; Gap x drop-off: 50; Expect: 10; Word Size: 11; and Filter: on. Identity is measured over the entire length of a sequence. Brenner et al. (1998; Proc Natl Acad Sci 95:6073–6078, incorporated herein by reference) analyzed BLAST for its ability to identify structural homologs by sequence identity and found 30% identity is a reliable threshold for sequence alignments of at least 150 residues and 40%, for alignments of at least 70 residues.

The cDNAs of this application were compared with assembled consensus sequences or templates found in the LIFESEQ GOLD database (Incyte Genomics). Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another, and those having local similarity of at least 82% were combined and reassembled. Bins having templates with less than 95% local identity were split. Templates were subjected to analysis by STITCHER/EXON MAPPER algorithms that determine the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leqq 1\times10^{-8}$. The templates were also subjected to frameshift FASTx against GENPEPT, and homolog match was defined as having an E-value of $\leqq 1\times10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/). The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Genethon are used to determine if any of the cDNAs presented in the Sequence Listing have been mapped. Any of the fragments of the cDNA encoding human presenilin variant that have been mapped result in the assignment of all related regulatory and coding sequences to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C. for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2× SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 $\mu$g. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807,522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigrna Aldrich) in 95% ethanol, and curing in a 110 C. oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C.; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 μl TE buffer, denaturing by heating to 100 C. for five min, and briefly centrifuging. The denatured cDNA is then added to a REDIPRIME tube (APB), gently mixed until blue color is evenly distributed, and briefly centrifuged. Five μl of [$^{32}$P]dCTP is added to the tube, and the contents are incubated at 37 C. for 10 min. The labeling reaction is stopped by adding 5 μl of 0.2M EDTA, and probe is purified from unincorporated nucleotides using a PROBEQUANT G-50 microcolumn (APB). The purified probe is heated to 100 C. for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 μl TE buffer and adding 5 11 5× buffer, 1 μl 0.1 M DTT, 3 μl Cy3 or Cy5 labeling mix, 1 μl RNase inhibitor, 1 μl reverse transcriptase, and 5 μl 1× yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNAm-differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C. for two hr. The reaction mixture is then incubated for 20 min at 85 C., and probes are purified using two successive CHROMA SPIN+TE 30 columns (Clontech, Palo Alto Calif.). Purified probe is ethanol precipitated by diluting probe to 90 μl in DEPC-treated water, adding 2 μl 1 mg/ml glycogen, 60 μl 5 M sodium acetate, and 300 μl 100% ethanol. The probe is centrifuged for 20 min at 20,800× g, and the pellet is resuspended in 12 μl resuspension buffer, heated to 65 C. for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M $Na_2HPO_4$, 5 mM EDTA, pH 7) at 55 C. for two hr. The probe, diluted in 15 ml fresh hybridization solution, is then added to the membrane. The membrane is hybridized with the probe at 55 C. for 16 hr. Following hybridization, the membrane is washed for 15 min at 25 C. in 1 mM Tris (pH 8.0), 1% Sarkosyl, and four times for 15 min each at 25 C. in 1 mM Tris (pH 8.0). To detect hybridization complexes, XOMAT-AR film (Eastman Kodak, Rochester N.Y.) is exposed to the membrane overnight at −70 C., developed, and examined visually.

Polymer Coated Slide-based Hybridization

Probe is heated to 65 C. for five min, centrifuged five min at 9400 rpm in a 5415C microcentrifuge (Eppendorf Scientific, Westbury N.Y.), and then 18 μl is aliquoted onto the array surface and covered with a coverslip. The arrays are transferred to a waterproof chamber having a cavity just slightly larger than a microscope slide. The chamber is kept at 100% humidity internally by the addition of 140 μl of 5× SSC in a corner of the chamber. The chamber containing the arrays is incubated for about 6.5 hr at 60 C. The arrays are washed for 10 min at 45 C. in 1× SSC, 0.1% SDS, and three times for 10 min each at 45 C. in 0.1× SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Filters positioned between the array and the photomultiplier tubes are used to separate the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Transcript Imaging

A transcript image was performed using the LIFESEQ GOLD database (Mar01rel, Incyte Genomics). This process allowed assessment of the relative abundance of the expressed polynucleotides in all of the cDNA libraries. Criteria for transcript imaging can be selected from category, number of cDNAs per library, library description, disease indication, clinical relevance of sample, and the like.

All sequences and cDNA libraries in the LIFESEQ database have been categorized by system, organ/tissue and cell type. For each category, the number of libraries in which the sequence was expressed were counted and shown over the total number of libraries in that category. In some transcript images, all normalized or pooled libraries, which have high copy number sequences removed prior to processing, and all mixed or pooled tissues, which are considered non-specific in that they contain more than one tissue type or more than one subject's tissue, can be excluded from the analysis. Cell lines and/or fetal tissue data can also be disregarded unless the elucidation of inherited disorders would be furthered by their inclusion in the analysis.

For example, transcript image for SEQ ID NO:2 in bladder tissue is shown below. The first column shows library name; the second column, the number of cDNAs sequenced in that library; the third column, the description of the library; the fourth column, absolute abundance of the transcript in the library; and the fifth column, percentage abundance of the transcript in the library.

Category: Urinary Tract

| Library* | cDNAs | Description of Library** | Abundance | % Abundance |
|---|---|---|---|---|
| BLADTUT02 | 3248 | tumor, TC CA, 80F, m/BLADNOT03 | 1 | 0.0308 |
| BLADTUT08 | 3625 | tumor, TC CA, 72M | 1 | 0.0276 |
| BLADTUT03 | 3870 | tumor, TC CA, 58M, m/BLADNOT09 | 1 | 0.0258 |

*All cell lines, fetal, mixed, pooled, normalized, and subtracted libraries have been removed from the analysis.

**Expression was not found in cytologically normal bladder samples used to construct BLADNOR01, BLADNOT01, BLADNOT03, BLADNOT04, BLADNOT08, and BLADNOT09

As can be seen from the transcript image, SEQ ID NO:2 was differentially expressed in transitional cell carcinoma of the bladder. In this case, the sequence was expressed in tumors and absent from cytologically normal tissues including the matched (m/) BLADNOT03 and BLADNOT09 shown above. When used with biopsied bladder samples, SEQ ID NO:2 is a specific diagnostic for transitional cell carcinoma. The tissue-specific differential expression of SEQ ID NO:2 in bladder makes it a useful and clinically relevant diagnostic marker for transitional cell carcinoma of the bladder.

IX Complementary Molecules

Molecules complementary to the cDNA, from about 5 (PNA) to about 5000 bp (complement of a cDNA insert), are used to detect or inhibit gene expression. Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if elements for inducing vector replication are used in the transformation/expression system.

Stable transformation of dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

X Expression of Human Presenilin Variant

Expression and purification of the protein are achieved using either a mammalian cell expression system or an insect cell expression system. The pUB6/V5-His vector system (Invitrogen, Carlsbad Calif.) is used to express human presenilin variant in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6× His) sequence for rapid purification on PROBOND resin (Invitrogen). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6× his which enables purification as described above. Purified protein is used in the following activity and to make antibodies.

XI Production of Antibodies

Human presenilin variant is purified using polyacrylamide gel electrophoresis and used to immunize mice or rabbits. Antibodies are produced using the protocols well known in the art and summarized below. Alternatively, the amino acid sequence of human presenilin variant is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an 431A peptide synthesizer (ABI) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIV Two-Hybrid Screen

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C. until the colonies have grown up and are counted. The colonies are pooled in a minimal volume of 1× TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of 13-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C. until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

XV Demonstration of Human Presenilin Variant Activity

Human presenilin variant activity may be demonstrated by the ability of human presenilin proteins to substitute for *C. elegans* SEL-12 protein in an assay to rescue an sel-12 mutant phenotype that displays reduced egg-laying properties. (Levitan et al. supra.) pLEX-based plasmid constructs are prepared containing SEL-12 or human presenilin variant and are injected into *C. elegans* cells containing the sel-12 (ar131) mutation that significantly reduces egg-laying activity. Egg-laying is assessed after 2 days and compared between control sel-12(ar131) cells, and the same cells transfected with the pLEX vector alone, the pLEX-SEL12, or the pLEX-human presenilin variant constructs. The difference in egg-laying activities between pLEX-human presenilin variant tranfected cells and control cells or cells transfected with the pLEX vector alone is a measure of presenilin activity in human presenilin variant.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. An isolated cDNA, or the complement thereof, comprising a nucleic acid sequence encoding a protein having and amino acid sequence of SEQ ID NO:1.

2. An isolated cDNA comprising a nucleic acid sequence selected from:

a) SEQ ID NO:2 or the complement thereof b) SEQ ID NO:5, or the complement thereof, and c) SEQ ID NO:6 or the complement thereof.

3. A composition comprising the cDNA of claim 1 and a labeling moiety.

4. A vector comprising the cDNA of claim 1.

5. A host cell comprising the vector of claim 4.

6. A method for using a cDNA to produce a protein, the method comprising:

a) culturing the host cell of claim 5 under conditions for protein expression; and b) recovering the protein having the amino acid sequence of SEQ ID NO:1 from the host cell culture.

7. A method for using a cDNA to detect expression of a nucleic acid in a sample comprising:

a) hybridizing the cDNA of claim 1 to the nucleic acids of the sample thereby forming hybridization complexes; and b) detecting complex formation, wherein complex formation indicates expression in the sample.

8. The method of claim 7 further comprising amplifying the nucleic acids of the sample prior to hybridization.

9. The method of claim 7 wherein the cDNA is attached to a substrate.

10. The method of claim 7 wherein complex formation is compared to at least one standard and is diagnostic of bladder transitional cell carcinoma.

11. A method of using a cDNA to screen a plurality of molecules or compounds, the method comprising:

a) combining the cDNA of claim 1 with a plurality of molecules or compounds under conditions to allow specific binding; and b) detecting specific binding, thereby identifying a molecule or compound which specifically binds the cDNA.

12. The method of claim 11 wherein the molecules or compounds are selected from DNA molecules, RNA molecules, peptides, and transcription factors.

* * * * *

SEQUENCE LISTING

```
<160> NUMBER OF SEQ ID NOS: 14

<210> SEQ ID NO 1
<211> LENGTH: 180
<212> TYPE: PRT
<213> ORGANISM: Homo sapiens
<220> FEATURE:
<221> NAME/KEY: misc_feature
<223> OTHER INFORMATION: Incyte ID No: 1353337CD1

<400> SEQUENCE: 1
```

-continued

```
Met Thr Glu Leu Pro Ala Pro Leu Ser Tyr Phe Gln Asn Ala Gln
  1               5                  10                  15

Met Ser Glu Asp Asn His Leu Ser Asn Thr Asn Asp Asn Arg Glu
                 20                  25                  30

Arg Gln Glu His Asn Asp Arg Arg Ser Leu Gly His Pro Glu Pro
                 35                  40                  45

Leu Ser Asn Gly Arg Pro Gln Gly Asn Ser Arg Gln Val Val Glu
                 50                  55                  60

Gln Asp Glu Glu Glu Asp Glu Glu Leu Thr Leu Lys Tyr Gly Ala
                 65                  70                  75

Lys His Val Ile Met Leu Phe Val Pro Val Thr Leu Cys Met Val
                 80                  85                  90

Val Val Val Ala Thr Ile Lys Ser Val Ser Phe Tyr Thr Arg Lys
                 95                 100                 105

Asp Gly Gln Leu Ile Tyr Thr Pro Phe Thr Glu Asp Thr Glu Thr
                110                 115                 120

Val Gly Gln Arg Ala Leu His Ser Ile Leu Asn Ala Ala Ile Met
                125                 130                 135

Ile Ser Val Ile Val Val Met Thr Ile Leu Leu Val Val Leu Tyr
                140                 145                 150

Lys Tyr Arg Cys Tyr Lys Val Ser Met Arg His Arg Ser Leu Leu
                155                 160                 165

Ser Thr Leu Phe Phe Leu Trp Leu Gly Ile Leu Val Thr Val Thr
                170                 175                 180


<210> SEQ ID NO 2
<211> LENGTH: 816
<212> TYPE: DNA
<213> ORGANISM: Homo sapiens
<220> FEATURE:
<221> NAME/KEY: misc_feature
<223> OTHER INFORMATION: Incyte ID No: 1353337CB1

<400> SEQUENCE: 2

gaacctgagc tacgagccgc ggcggcagcg gggcggcggg gaagcgtata cctaatctgg      60

gagcctgcaa gtgacaacag cctttgcggt ccttagacag cttggcctgg aggagaacac     120

atgaaagaaa gaacctcaag aggctttgtt ttctgtgaaa cagtatttct atacagttgc     180

tccaatgaca gagttacctg caccgttgtc ctacttccag aatgcacaga tgtctgagga     240

caaccacctg agcaatacta atgacaatag agaacggcag gagcacaacg acagacggag     300

ccttggccac cctgagccat tatctaatgg acgaccccag ggtaactccc ggcaggtggt     360

ggagcaagat gaggaagaag atgaggagct gacattgaaa tatggcgcca agcatgtgat     420

catgctcttt gtccctgtga ctctctgcat ggtggtggtc gtggctacca ttaagtcagt     480

cagcttttat acccggaagg atgggcagct aatctatacc ccattcacag aagataccga     540

gactgtgggc cagagagccc tgcactcaat tctgaatgct gccatcatga tcagtgtcat     600

tgttgtcatg actatcctcc tggtggttct gtataaatac aggtgctata aggtgagcat     660

gagacacaga tctttgcttt ccaccctgtt cttcttatgg ttgggtattc ttgtcacagt     720

aacttaactg atctaggaaa gaaaaaatgt tttgtcttct agagataagt taatttttag     780

ttttcttcct cctcattgtg gaacattcca aaaaaa                               816


<210> SEQ ID NO 3
<211> LENGTH: 493
```

-continued

<212> TYPE: DNA
<213> ORGANISM: Homo sapiens
<220> FEATURE:
<221> NAME/KEY: misc_feature
<223> OTHER INFORMATION: Incyte ID No: 991723R6
<221> NAME/KEY: unsure
<222> LOCATION: 458
<223> OTHER INFORMATION: a, t, c, g, or other

<400> SEQUENCE: 3
cccagaggaa aggggagtaa aacttggatt gggagatttc attttctaca gtgttctggt 60
tggtaaagcc tcagcaacag ccagtggaga ctggaacaca accatagcct gtttcgtagc 120
catattaatt ggtttgtgcc ttacattatt actccttgcc attttcaaga aagcattgcc 180
agctcttcca atctccatca cctttgggct tgttttctac tttgccacag attatcttgt 240
acagcctttt atggaccaat tagcattcca tcaattttat atctagcata tttgcggtta 300
gaatcccatg gatgtttctt ctttgactat aacaaaatct ggggaggaca aaggtgattt 360
tcctgtgtcc acatctaaca aagtcaagat tcccggctgg acttttgcag cttccttcca 420
agtcttcctg accaccttgc actattggac tttggaanga ggtgccatag aaaacgattt 480
gaacatactt cat 493

<210> SEQ ID NO 4
<211> LENGTH: 269
<212> TYPE: DNA
<213> ORGANISM: Homo sapiens
<220> FEATURE:
<221> NAME/KEY: misc_feature
<223> OTHER INFORMATION: Incyte ID No: 1353337H1

<400> SEQUENCE: 4
gggtaactcc cggcaggtgg tggagcaaga tgaggaagaa gatgaggagc tgacattgaa 60
atatggcgcc aagcatgtga tcatgctctt tgtccctgtg actctctgca tggtggtggt 120
cgtggctacc attaagtcag tcagctttta tacccggaag gatgggcagc taatctatac 180
cccattcaca gaagataccg agactgtggg ccagagagcc ctgcactcaa ttctgaatgc 240
tgccatcatg atcagtgtca ttgttgtca 269

<210> SEQ ID NO 5
<211> LENGTH: 356
<212> TYPE: DNA
<213> ORGANISM: Homo sapiens
<220> FEATURE:
<221> NAME/KEY: misc_feature
<223> OTHER INFORMATION: Incyte ID No: 1353337T6
<221> NAME/KEY: unsure
<222> LOCATION: 314, 352
<223> OTHER INFORMATION: a, t, c, g, or other

<400> SEQUENCE: 5
acttatctct agaagacaaa acattttttc tttcctagat cagttaagtt actgtgacaa 60
gaatacccaa ccataagaag aacagggtgg aaagcaaaga tctgtgtctc atgctcacct 120
tatagcacct gtatttatac agaaccacca ggaggatagt catgacaaca atgacactga 180
tcatgatggc agcattcaga attgagtgca gggctctctg gcccacagtc tcggtatctt 240
ctgtgaatgg ggtatagatt agctgcccat ccttccgggt ataaaagctg actgacttaa 300
tggtagccac gacnaccacc atgcagagag tcacagggac aaagagcatg ancaca 356

<210> SEQ ID NO 6

-continued

<211> LENGTH: 469
<212> TYPE: DNA
<213> ORGANISM: Homo sapiens
<220> FEATURE:
<221> NAME/KEY: misc_feature
<223> OTHER INFORMATION: Incyte ID No: 1353337F6

<400> SEQUENCE: 6

```
gggtaactcc cggcaggtgg tggagcaaga tgaggaagaa gatgaggagc tgacattgaa     60
atatggcgcc aagcatgtga tcatgctctt tgtccctgtg actctctgca tggtggtggt    120
cgtggctacc attaagtcag tcagctttta tacccggaag gatgggcagc taatctatac    180
cccattcaca gaagataccg agactgtggg ccagagagcc ctgcactcaa ttctgaatgc    240
tgccatcatg atcagtgtca ttgttgtcat gactatcctc ctggtggttc tgtataaata    300
caggtgctat aaggtgagca tgagacacag atctttgctt tccaccctgt tcttcttatg    360
gttgggtatt cttgtcacag taacttaact gatctaggaa agaaaaaatg ttttgtcttc    420
tagagataag ttaattttta gtttcttcct cctcattgtg gaacattcc                469
```

<210> SEQ ID NO 7
<211> LENGTH: 292
<212> TYPE: DNA
<213> ORGANISM: Homo sapiens
<220> FEATURE:
<221> NAME/KEY: misc_feature
<223> OTHER INFORMATION: Incyte ID No: 3555771H1

<400> SEQUENCE: 7

```
cagctccggg gtccgcggtt tcacatcgga aacaaaacag cggctggtct ggaaggaacc     60
tgagctacga gccgcggcgg cagcggggcg gcggggaagc gtatacctaa tctgggagcc    120
tgcaagtgac aacagccttt gcggtcctta gacagcttgg cctggaggag aacacatgac    180
agacagaacc tcaagaggct ttgttttctg tgaaacagta tttctataca gttgctccaa    240
tgacagagtt acctgcaccg ttgtcctact tccagaatgc acagatgtct ga            292
```

<210> SEQ ID NO 8
<211> LENGTH: 624
<212> TYPE: DNA
<213> ORGANISM: Canis familiaris
<220> FEATURE:
<221> NAME/KEY: misc_feature
<223> OTHER INFORMATION: Incyte ID No: 702764613H1

<400> SEQUENCE: 8

```
gaagtgtgtg acgagaggac atccctgatg tcggctgaga gccccccgcc acgctgctgc     60
caggaggcca ggcagggcct ggaggatgga gaaaatgctg cccagtggag aagccaggac    120
agcgaggagg actttgagga tgatgctgac cactacgtct gcggcggggt acctgggcag    180
ccgtcgggcc tggaggagga gctgaccctc aagtatgggg caaagcacgt gatcatgctc    240
tttgtgccgg tcaccctgtg catgattgtg gtggtggcca ccatcaagtc cgtgcgcttc    300
tacacagaga agaacggaca gctgccctat ggagcaggca gggagcagag cctgcagccc    360
gccatctccc tcagcatcta cacaccattc accgaggaca cgccctctgt gggccagcgc    420
ctcctcaact ctgtgctcaa caccctcatc atgatcagcg tcattgtggc catgaccatc    480
ttcttggtcg tgctctacaa gtaccgctgc tacaagttta tccatggctg gttgatcatg    540
tcatccttga tgctcctgtt ccttttcacc tatatctacc tcggggaagt gcttaagacc    600
tacaacgtgg ccatggacta ccta                                           624
```

<210> SEQ ID NO 9
<211> LENGTH: 231
<212> TYPE: DNA
<213> ORGANISM: Mus musculus
<220> FEATURE:
<221> NAME/KEY: misc_feature
<223> OTHER INFORMATION: Incyte ID No: 055263_Mm.1

<400> SEQUENCE: 9
gctccgtggg ccgcgagtat tcgtcggaaa caaaacagcg gcagctgatg cggaaaccta 60
ggctgcgagc cggccgcccg tgcgcggaga gagaaggaac caacacaaga cagcagccct 120
tcgaggtctt taggcagctt ggaggagaac acatgagaga aagaatccca agaggttttg 180
ttttctttga gaaggtattt ctgtccagct gctccaatga cagagatacc t 231

<210> SEQ ID NO 10
<211> LENGTH: 315
<212> TYPE: DNA
<213> ORGANISM: Rattus norvegicus
<220> FEATURE:
<221> NAME/KEY: misc_feature
<223> OTHER INFORMATION: Incyte ID No: 701725602H1

<400> SEQUENCE: 10
atagcctggc cacctcacta gcccctttc ccaagacctt gccgctctca cacagacagc 60
agatgggaag ttttagtttg aggcactttt gccaatctca ggtagagcag tgtgtgtaag 120
ggtctcaagt gtgacgtgtg tatagtaaca agatgaggag gaagacgaag agctgacatt 180
gaaatatgga gccaagcacg tcatcatgct ctttgttcct gtgaccctct gcatggtcgt 240
tgtggtggcc accatcaagt cagtcagctt ctacacccgg aaggatgggc agctaatcta 300
taccccattc acaga 315

<210> SEQ ID NO 11
<211> LENGTH: 112
<212> TYPE: DNA
<213> ORGANISM: Rattus norvegicus
<220> FEATURE:
<221> NAME/KEY: misc_feature
<223> OTHER INFORMATION: Incyte ID No: 701529589H1

<400> SEQUENCE: 11
gctgcccggg cgcggagagc gaaggaacca atacaagaca gcagcccttc gaggatctta 60
ggcagcttgg cctggaggag aacacatgag agaaagaatc cccagaggct tt 112

<210> SEQ ID NO 12
<211> LENGTH: 463
<212> TYPE: PRT
<213> ORGANISM: Homo sapiens
<220> FEATURE:
<221> NAME/KEY: misc_feature
<223> OTHER INFORMATION: Incyte ID No: g1244638

<400> SEQUENCE: 12

Met Thr Glu Leu Pro Ala Pro Leu Ser Tyr Phe Gln Asn Ala Gln
1 5 10 15

Met Ser Glu Asp Asn His Leu Ser Asn Thr Asn Asp Asn Arg Glu
20 25 30

Arg Gln Glu His Asn Asp Arg Arg Ser Leu Gly His Pro Glu Pro
35 40 45

Leu Ser Asn Gly Arg Pro Gln Gly Asn Ser Arg Gln Val Val Glu

-continued

```
                50                  55                  60

Gln Asp Glu Glu Glu Asp Glu Glu Leu Thr Leu Lys Tyr Gly Ala
                65                  70                  75

Lys His Val Ile Met Leu Phe Val Pro Val Thr Leu Cys Met Val
                80                  85                  90

Val Val Val Ala Thr Ile Lys Ser Val Ser Phe Tyr Thr Arg Lys
                95                 100                 105

Asp Gly Gln Leu Ile Tyr Thr Pro Phe Thr Glu Asp Thr Glu Thr
               110                 115                 120

Val Gly Gln Arg Ala Leu His Ser Ile Leu Asn Ala Ala Ile Met
               125                 130                 135

Ile Ser Val Ile Val Val Met Thr Ile Leu Leu Val Val Leu Tyr
               140                 145                 150

Lys Tyr Arg Cys Tyr Lys Val Ile His Ala Trp Leu Ile Ile Ser
               155                 160                 165

Ser Leu Leu Leu Leu Phe Phe Phe Ser Phe Ile Tyr Leu Gly Glu
               170                 175                 180

Val Phe Lys Thr Tyr Asn Val Ala Val Asp Tyr Ile Thr Val Ala
               185                 190                 195

Leu Leu Ile Trp Asn Phe Gly Val Val Gly Met Ile Ser Ile His
               200                 205                 210

Trp Lys Gly Pro Leu Arg Leu Gln Gln Ala Tyr Leu Ile Met Ile
               215                 220                 225

Ser Ala Leu Met Ala Leu Val Phe Ile Lys Tyr Leu Pro Glu Trp
               230                 235                 240

Thr Ala Trp Leu Ile Leu Ala Val Ile Ser Val Tyr Asp Leu Val
               245                 250                 255

Ala Val Leu Cys Pro Lys Gly Pro Leu Arg Met Leu Val Glu Thr
               260                 265                 270

Ala Gln Glu Arg Asn Glu Thr Leu Phe Pro Ala Leu Ile Tyr Ser
               275                 280                 285

Ser Thr Met Val Trp Leu Val Asn Met Ala Glu Gly Asp Pro Glu
               290                 295                 300

Ala Gln Arg Arg Val Ser Lys Asn Ser Lys Tyr Asn Ala Glu Ser
               305                 310                 315

Thr Glu Arg Glu Ser Gln Asp Thr Val Ala Glu Asn Asp Asp Gly
               320                 325                 330

Gly Phe Ser Glu Glu Trp Glu Ala Gln Arg Asp Ser His Leu Gly
               335                 340                 345

Pro His Arg Ser Thr Pro Glu Ser Arg Ala Ala Val Gln Glu Leu
               350                 355                 360

Ser Ser Ser Ile Leu Ala Gly Glu Asp Pro Glu Glu Arg Gly Val
               365                 370                 375

Lys Leu Gly Leu Gly Asp Phe Ile Phe Tyr Ser Val Leu Val Gly
               380                 385                 390

Lys Ala Ser Ala Thr Ala Ser Gly Asp Trp Asn Thr Thr Ile Ala
               395                 400                 405

Cys Phe Val Ala Ile Leu Ile Gly Leu Cys Leu Thr Leu Leu Leu
               410                 415                 420

Leu Ala Ile Phe Lys Lys Ala Leu Pro Ala Leu Pro Ile Ser Ile
               425                 430                 435

Thr Phe Gly Leu Val Phe Tyr Phe Ala Thr Asp Tyr Leu Val Gln
               440                 445                 450
```

-continued

Pro Phe Met Asp Gln Leu Ala Phe His Gln Phe Tyr Ile
455 460

<210> SEQ ID NO 13
<211> LENGTH: 1392
<212> TYPE: DNA
<213> ORGANISM: Homo sapiens
<220> FEATURE:
<221> NAME/KEY: misc_feature
<223> OTHER INFORMATION: Incyte ID No: g1244637

<400> SEQUENCE: 13
atgacagagt tacctgcacc gttgtcctac ttccagaatg cacagatgtc tgaggacaac 60
cacctgagca atactaatga caatagagaa cggcaggagc acaacgacag acggagcctt 120
ggccaccctg agccattatc taatggacga ccccagggta actcccggca ggtggtggag 180
caagatgagg aagaagatga ggagctgaca ttgaaatatg gcgccaagca tgtgatcatg 240
ctctttgtcc ctgtgactct ctgcatggtg gtggtcgtgg ctaccattaa gtcagtcagc 300
ttttataccc ggaaggatgg gcagctaatc tataccccat tcacagaaga taccgagact 360
gtgggccaga gagccctgca ctcaattctg aatgctgcca tcatgatcag tgtcattgtt 420
gtcatgacta tcctcctggt ggttctgtat aaatacaggt gctataaggt catccatgcc 480
tggcttatta tatcatctct attgttgctg ttcttttttt cattcattta cttgggggaa 540
gtgtttaaaa cctataacgt tgctgtggac tacattactg ttgcactcct gatctggaat 600
tttggtgtgg tgggaatgat ttccattcac tggaaaggtc cacttcgact ccagcaggca 660
tatctcatta tgattagtgc cctcatggcc ctggtgttta tcaagtacct ccctgaatgg 720
actgcgtggc tcatcttggc tgtgatttca gtatatgatt tagtggctgt tttgtgtccg 780
aaaggtccac ttcgtatgct ggttgaaaca gcccaggaga gaaatgaaac gctttttcca 840
gctctcattt actcctcaac aatggtgtgg ttggtgaata tggcagaagg agacccggaa 900
gctcaaagga gagtatccaa aaattccaag tataatgcag aaagcacaga aagggagtca 960
caagacactg ttgcagagaa tgatgatggc gggttcagtg aggaatggga agcccagagg 1020
gacagtcatc tagggcctca tcgctctaca cctgagtcac gagctgctgt ccaggaactt 1080
tccagcagta tcctcgctgg tgaagaccca gaggaaaggg gagtaaaact tggattggga 1140
gatttcattt tctacagtgt tctggttggt aaagcctcag caacagccag tggagactgg 1200
aacacaacca tagcctgttt cgtagccata ttaattggtt tgtgccttac attattactc 1260
cttgccattt tcaagaaagc attgccagct cttccaatct ccatcacctt tgggcttgtt 1320
ttctactttg ccacagatta tcttgtacag ccttttatgg accaattagc attccatcaa 1380
ttttatatct ag 1392

<210> SEQ ID NO 14
<211> LENGTH: 467
<212> TYPE: PRT
<213> ORGANISM: Homo sapiens
<220> FEATURE:
<221> NAME/KEY: misc_feature
<223> OTHER INFORMATION: Incyte ID No: g1709856

<400> SEQUENCE: 14

Met Thr Glu Leu Pro Ala Pro Leu Ser Tyr Phe Gln Asn Ala Gln
1 5 10 15

Met Ser Glu Asp Asn His Leu Ser Asn Thr Val Arg Ser Gln Asn

-continued

```
                20                  25                  30

Asp Asn Arg Glu Arg Gln Glu His Asn Asp Arg Arg Ser Leu Gly
                35                  40                  45

His Pro Glu Pro Leu Ser Asn Gly Arg Pro Gln Gly Asn Ser Arg
                50                  55                  60

Gln Val Val Glu Gln Asp Glu Glu Glu Asp Glu Glu Leu Thr Leu
                65                  70                  75

Lys Tyr Gly Ala Lys His Val Ile Met Leu Phe Val Pro Val Thr
                80                  85                  90

Leu Cys Met Val Val Val Val Ala Thr Ile Lys Ser Val Ser Phe
                95                  100                 105

Tyr Thr Arg Lys Asp Gly Gln Leu Ile Tyr Thr Pro Phe Thr Glu
                110                 115                 120

Asp Thr Glu Thr Val Gly Gln Arg Ala Leu His Ser Ile Leu Asn
                125                 130                 135

Ala Ala Ile Met Ile Ser Val Ile Val Val Met Thr Ile Leu Leu
                140                 145                 150

Val Val Leu Tyr Lys Tyr Arg Cys Tyr Lys Val Ile His Ala Trp
                155                 160                 165

Leu Ile Ile Ser Ser Leu Leu Leu Leu Phe Phe Phe Ser Phe Ile
                170                 175                 180

Tyr Leu Gly Glu Val Phe Lys Thr Tyr Asn Val Ala Val Asp Tyr
                185                 190                 195

Ile Thr Val Ala Leu Leu Ile Trp Asn Phe Gly Val Val Gly Met
                200                 205                 210

Ile Ser Ile His Trp Lys Gly Pro Leu Arg Leu Gln Gln Ala Tyr
                215                 220                 225

Leu Ile Met Ile Ser Ala Leu Met Ala Leu Val Phe Ile Lys Tyr
                230                 235                 240

Leu Pro Glu Trp Thr Ala Trp Leu Ile Leu Ala Val Ile Ser Val
                245                 250                 255

Tyr Asp Leu Val Ala Val Leu Cys Pro Lys Gly Pro Leu Arg Met
                260                 265                 270

Leu Val Glu Thr Ala Gln Glu Arg Asn Glu Thr Leu Phe Pro Ala
                275                 280                 285

Leu Ile Tyr Ser Ser Thr Met Val Trp Leu Val Asn Met Ala Glu
                290                 295                 300

Gly Asp Pro Glu Ala Gln Arg Arg Val Ser Lys Asn Ser Lys Tyr
                305                 310                 315

Asn Ala Glu Ser Thr Glu Arg Glu Ser Gln Asp Thr Val Ala Glu
                320                 325                 330

Asn Asp Asp Gly Gly Phe Ser Glu Glu Trp Glu Ala Gln Arg Asp
                335                 340                 345

Ser His Leu Gly Pro His Arg Ser Thr Pro Glu Ser Arg Ala Ala
                350                 355                 360

Val Gln Glu Leu Ser Ser Ser Ile Leu Ala Gly Glu Asp Pro Glu
                365                 370                 375

Glu Arg Gly Val Lys Leu Gly Leu Gly Asp Phe Ile Phe Tyr Ser
                380                 385                 390

Val Leu Val Gly Lys Ala Ser Ala Thr Ala Ser Gly Asp Trp Asn
                395                 400                 405

Thr Thr Ile Ala Cys Phe Val Ala Ile Leu Ile Gly Leu Cys Leu
                410                 415                 420
```

-continued

```
Thr Leu Leu Leu Leu Ala Ile Phe Lys Lys Ala Leu Pro Ala Leu
                425                 430                 435

Pro Ile Ser Ile Thr Phe Gly Leu Val Phe Tyr Phe Ala Thr Asp
                440                 445                 450

Tyr Leu Val Gln Pro Phe Met Asp Gln Leu Ala Phe His Gln Phe
                455                 460                 465

Tyr Ile
```